US006916940B2

(12) United States Patent
Kirsch et al.

(10) Patent No.: US 6,916,940 B2
(45) Date of Patent: Jul. 12, 2005

(54) METHOD FOR PRODUCING CYCLIC CARBOXYLIC ORTHOESTER FLUORIDES AND CORRESPONDING COMPOUNDS

(75) Inventors: Peer Kirsch, Darmstadt (DE); Andreas Taugerbeck, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 118 days.

(21) Appl. No.: 10/399,536

(22) PCT Filed: Oct. 1, 2001

(86) PCT No.: PCT/EP01/11323

§ 371 (c)(1),
(2), (4) Date: Apr. 18, 2003

(87) PCT Pub. No.: WO02/34740

PCT Pub. Date: May 2, 2002

(65) Prior Publication Data

US 2004/0054196 A1 Mar. 18, 2004

(30) Foreign Application Priority Data

Oct. 20, 2000 (EP) .......................................... 00122844
Feb. 2, 2001 (DE) .......................................... 101 05 313

(51) Int. Cl.[7] .................... C07D 321/00; C07D 321/10; C07D 321/12; C07D 323/00; C07D 319/12

(52) U.S. Cl. ........................ 549/348; 549/380; 549/455

(58) Field of Search ................................ 549/348, 380, 549/455

(56) References Cited

U.S. PATENT DOCUMENTS 5,235,074 A * 8/1993 Navarrini et al. ........... 549/449
5,789,580 A 8/1998 Chambers et al.
6,787,062 B2 * 9/2004 Kirsch et al. .......... 252/299.63

FOREIGN PATENT DOCUMENTS

WO WO 96 03357 A 2/1996
WO WO 01 64667 A 9/2001

OTHER PUBLICATIONS

Bayliff et al, "Polyhalogenoheterocyclic Compounds. Part 38. Reactions of Fluorinated–Alkenes and –Cycloalkenes with Difunctional Nucleophiles" J. Chem. Soc. Perkin Trans. vol. 4, pp. 763–767 (1987).*

Muffler, H.: "Cylisterung unter Beteiligung bon Fluridionen." Journal of Fluorine Chemistry, Bd. 21, Nr. 2, 1962.

Sondeg S C et al., "Gem–Difluoro compounds: a convenient preparation from ketones and aldehydes by halogen fluoride treatment of 1,3–dithalolanes" Journal of Organic Chemistry, American Chemical Society., Easton, US, Bd. 51, 1986.

* cited by examiner

*Primary Examiner*—Richard L. Raymond
*Assistant Examiner*—Zachary C. Tucker
(74) *Attorney, Agent, or Firm*—Millen White Zelano & Branigan, P.C.

(57) ABSTRACT

The invention relates to a process for the preparation of cyclic carboxylic acid orthoester fluorides in which a) at least one bis(alkylthio)carbenium salt is reacted with at least one organic compound containing at least two hydroxyl groups in the presence of at least one base,
b) and subsequently, preferably in situ, the resultant thioorthoester is subjected to oxidative fluorodesulfurisation using a fluorinating agent and an oxidant to give the cyclic carboxylic acid orthoester fluoride.

15 Claims, No Drawings

METHOD FOR PRODUCING CYCLIC CARBOXYLIC ORTHOESTER FLUORIDES AND CORRESPONDING COMPOUNDS

The invention relates to a process for the preparation of cyclic carboxylic acid orthoester fluorides, and to novel cyclic carboxylic acid orthoester fluorides obtainable by the process according to the invention.

Cyclic carboxylic acid orthoester fluorides can be used, in particular, as structural constituents of liquid crystals, pharmaceuticals, crop-protection compositions or as precursors for such products or for the preparation of polymers.

The few processes known hitherto for the preparation of carboxylic acid orthoester fluorides are based either on acid-catalysed replacement of alkoxy or acyloxy functions in orthoester derivatives by fluorine (G. Simchen, "Orthocarbonsäure-Derivate" [Orthocarboxylic Acid Derivatives] in Houben-Weyl: Methoden der Organischen Chemie [Methods of Organic Chemistry], Georg Thieme Verlag, Stuttgart, 1985, pp. 54–63) or on the reaction of diols with perfluoroolefins (Bayliff et al., J. Chem. Soc., Perkin Trans. I, 1987, 763–767). By contrast, no generally applicable process for the preparation of cyclic carboxylic acid orthoester fluorides has been disclosed.

It is therefore an object of the invention to provide a process for the preparation of cyclic carboxylic acid orthoester fluorides which starts from readily accessible starting materials, does not require isolation of intermediates, and gives the products in good yields.

A further object of the invention is to describe novel products obtainable by the process according to the invention and to indicate advantageous uses of these products.

The object is achieved by a process according to claim 1. The sub-claims relate to advantageous variants of this process.

The invention thus relates to a process of the type mentioned at the outset, in which a) at least one bis(alkylthio)carbenium salt is reacted with at least one organic compound containing at least two hydroxyl groups in the presence of at least one base, b) and subsequently, preferably in situ, the resultant thioorthoester is subjected to oxidative fluorodesulfurisation using a fluorinating agent and an oxidant to give the cyclic carboxylic acid orthoester fluoride.

An advantage of the process according to the invention is the ready accessibility of the bis(alkylthio)carbenium salts and the hydroxyl compounds, in particular the diols, as starting compounds.

Furthermore, the oxidative fluorodesulfurisation is carried out under very mild, slightly basic conditions and is therefore, in contrast to the conventional methods, compatible with a multiplicity of unprotected functional groups, for example a nitrile group.

A further particular advantage of the process according to the invention is that the reaction starting from the carbenium salt and the hydroxyl compound to the product can be carried out in a reaction mixture, i.e. without isolation and purification of the intermediates. The yields that can be achieved here are high with low by-product formation.

The invention furthermore relates to novel cyclic carboxylic acid orthoester fluorides obtainable by the process according to the invention, in particular those according to claims 11 and 12. These compounds can be used as structural constituents of liquid crystals, pharmaceuticals, agrochemicals or polymers. A further area of application is use as chiral component or dopant in liquid-crystal mixtures or polymers. These orthoester fluorides can also be used in the presence of one or more Lewis or Brönstedt acids as 1,1-dialkoxyalkylating agents for the preparation of cyclic ketals or cyclic orthocarboxylic acid esters.

Preferred variants of the process according to the invention are described below.

The process according to the invention is preferably carried out using a bis(alkylthio)carbenium salt of the formula II.

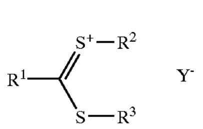

II

In this formula:

$R^1$ is straight-chain, branched or cyclic alkyl having from 1 to 25 carbon atoms, in which one or more H atoms may be replaced by halogen, —CN or further optionally substituted alkyl and/or aryl radicals, and/or in which one or more non-adjacent —$CH_2$— groups may be replaced, independently of one another, by —CO—, —O—CO—, —CO—O—, —O—, —S—, —CH═CH—, —C≡C—, —NH— or —$N(CH_3)$—, and/or aryl, which may be monosubstituted or polysubstituted by halogen or straight-chain, branched and/or cyclic alkyl and/or aryl, and in which one or more CH groups may be replaced by N or O, $R^2$ and $R^3$, independently of one another, are straight-chain, branched or cyclic alkyl having from 1 to 12 carbon atoms, where $R^2$ and $R^3$ may be bridged to one another in such a way that the group

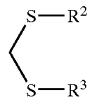

is a 4- to 8-membered ring, and/or in which one or more H atoms may be replaced by halogen or further optionally substituted alkyl and/or aryl radicals, and/or in which one or more non-adjacent —$CH_2$— groups may be replaced, independently of one another, by —CO—, —O—, —S—, —CH═CH—, —C≡C—, —NH— or —$N(CH_3)$—, and/or aryl, which may be monosubstituted or polysubstituted by halogen or straight-chain, branched and/or cyclic alkyl and/or aryl, and $Y^-$ is a non-coordinating or weakly coordinating anion, $R^2$ and $R^3$ are preferably bridged to one another in such a way that the

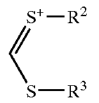

group is in the form of a 5- to 7-membered ring

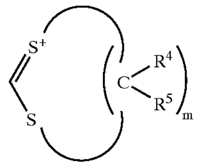

in which $R^4$ and $R^5$ are H or an optionally substituted alkyl or alkenyl group having from 1 to 6 carbon atoms, where the group

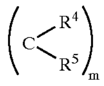

may form a cycloalkyl or aryl group, and m is 2, 3 or 4.

The process according to the invention is preferably carried out using an organic compound containing at least two hydroxyl groups of the formula III

III

In this formula:

W is a straight-chain, branched or cyclic alkylene group having 2 or more carbon atoms, in which one or more H atoms may be replaced by halogen or further optionally substituted alkyl and/or aryl radicals, and/or in which one or more non-adjacent —$CH_2$— groups may be replaced, independently of one another, by —CO—, —O—, —S—, —CH═CH—, —C≡C—, —NH— or —$N(CH_3)$—, and/or an arylene group, which may be monosubstituted or polysubstituted by halogen or straight-chain, branched and/or cyclic alkyl and/or aryl, and in which one or more CH groups may be replaced by N or O.

The reaction of a bis(alkylthio)carbenium salt of the formula II with an organic compound containing at least two hydroxyl groups of the formula III gives, in accordance with the invention, a cyclic carboxylic acid orthoester fluoride of the formula I

I

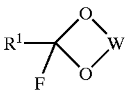

in which $R^1$ and W are as defined above.

Preferred hydroxyl compounds of the formula III are those which, when employed in the process according to the invention, are capable of forming cyclic carboxylic acid orthoester fluorides, in particular having 5, 6, 7 or 8 atoms in the orthoester ring. To this end, the group W in the compound of the formula III preferably has, between the two hydroxyl groups, a chain length of 2, 3, 4 or 5 atoms, which may be part of a straight-chain, branched or cyclic aliphatic, aromatic or heteroaromatic group.

The organic compound containing at least two hydroxyl groups is preferably an alkanediol, an aromatic or heteroaromatic dihydroxyl compound, in particular 1,2-dihydroxybenzene, 2,2'-dihydroxy-1,1'-biphenyl, 2,2'-dihydroxy-1,1'-binaphthyl, 7,7'-dihydroxy-1,1'-binaphthyl or 8,8'-dihydroxy-1,1'-binaphthyl, or a hydroxyalkylphenol, in particular salicyl alcohol, which may be substituted by one or more halogen atoms and/or alkyl groups. Preferred alkanediols are ethane-1,2-diol, propane-1,3-diol or 2,2-dimethylpropane-1,3-diol, which may also be monosubstituted or polysubstituted by fluorine and/or chlorine. Preferred halogenated alkanediols are $HOCH_2CF_2CH_2OH$, $HOCH_2CF_2CF_2CH_2OH$, $HOCH_2CF(CF_3)CH_2OH$, $HOCH_2C(CF_3)_2CH_2OH$, $HOCH_2CHFCH_2OH$ or $HOCH_2CCl_2CH_2OH$.

In the bis(alkylthio)carbenium salt of the formula II, $Y^-$ is preferably a halide, tetrafluoroborate, hexafluorophosphate, perchlorate or alkyl- or arylcarboxylate or alkyl- or arylsulfonate anion, where one, a number or all of the H atoms in the alkyl or aryl groups may be substituted by fluorine or chlorine.

The oxidants used may be conventional oxidants. The oxidant employed is preferably a compound which liberates halonium equivalents. Examples of oxidants are N-chlorosuccinimide, N-bromosuccinimide, N-iodosuccinimide, dibromoisocyanuric acid, 1,3-dibromo-5,5-dimethylhydantoin, chlorine and bromine. Particular preference is given to bromine, since the bromides formed can easily be separated off. Likewise suitable are $SO_2Cl_2$, $SO_2ClF$, chloramine-T, nitrosonium and nitronium salts, for example $NO^+BF_4^-$. The nitrosonium and nitronium salts may, if desired, also be prepared in situ from suitable precursors, for example from inorganic or organic nitrites and/or nitrates.

The fluorinating agents employed may be conventional fluorinating agents. The fluorinating agent is particularly preferably selected from the group formed by hydrogen fluoride, aliphatic and aromatic amine/hydrogen fluoride complexes, in particular selected from the group formed by pyridine, triethylamine, melamine and polyvinylpyridine/hydrogen fluoride complexes.

When carrying out the process according to the invention, the bis(alkylthio)carbenium salt is preferably employed in a molar ratio of less than or equal to 2:1, in particular less than or equal to 1.7:1, particularly preferably less than or equal to 1.3:1, very particularly preferably less than or equal to 1:1, to the organic compound containing at least two hydroxyl groups. The use of the carbenium salt in an approximately equimolar or sub-stoichiometric amount with respect to the hydroxyl compound generally results in formation of less by-products. Thus, at molar ratios in the range greater than or equal to 2:1, compounds containing one or two $CF_2O$ bridges can form through addition of in each case one bis(alkylthio)carbenium ion onto a hydroxyl group via dithioorthoesters as intermediates and subsequent fluorodesulfurisation.

An example of the way the process according to the invention is carried out is indicated below. A solution of the hydroxyl compound and at least one base is added to a solution of the bis(alkylthio)carbenium salt, preferably at a temperature in the range from −100 to +50° C. Advantageously suitable bases for this purpose are organic nitrogen bases, in particular tertiary aliphatic and/or aromatic amines, such as, for example, triethylamine, pyridine or pyridine derivatives. The base is advantageously employed in a molar ratio of from 1:1 to 2:1, based on the hydroxyl compound. Suitable solvents are, in particular, polar solvents or solvent mixtures, for example ethers or haloalkanes, such as diethyl ether, tetrahydrofuran, dichloromethane and/or trichloromethane.

Intermediates, such as thioorthoesters, formed by reaction of the bis(alkylthio)carbenium salts with the hydroxyl compounds are generally not isolated, but are subjected directly to oxidative desulfurisation in the reaction mixture to give the cyclic carboxylic acid orthoester fluoride.

To this end, the fluorinating agent and the oxidant are added to the reaction mixture. The temperature of the mixture is advantageously then increased, for example to from −20° C. to 50° C. The cyclic carboxylic acid orthoester fluoride can be obtained from the reaction mixture by methods familiar to the person skilled in the art, for example by recrystallisation and/or chromatography.

The bis(alkylthio)carbenium salts as starting materials in the process according to the invention are readily accessible by known methods, for example by condensation of carboxylic acids or activated carboxylic acid derivatives with dithiols. These are particularly advantageously obtained by addition of an acid onto a ketene dithioketal. Thus, the bis(alkylthio)carbenium salt of the formula II is obtainable by addition of an acid HY, in which Y is as defined above, onto a ketene dithioketal of the formula IV

IV

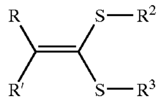

.

In the formula IV, $R^2$ and $R^3$ are as defined above, and R and R' have, independently of one another, one of the meanings indicated above for $R^1$, including H, in such a way that the group

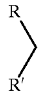

has the same meaning as $R^1$.

The acid is employed in an approximately equimolar amount, based on the ketene dithioketal units to be reacted. The reaction with the acid HY is advantageously carried out at a temperature in the range of from −80 to +30° C. in an inert polar solvent or solvent mixture, as already mentioned above by way of example. Particularly preferred acids HY here are trifluoromethanesulfonic acid and a tetrafluoroboric acid/diethyl ether complex.

An advantage of this process variant starting from ketene dithioketal is the fact that the addition of acid onto the ketene dithioketals can be carried out even under very mild conditions. This gives access to bis(alkylthio)carbenium salts which contain sensitive functional groups, such as esters, nitriles or ketals.

Furthermore, this variant has the advantage that the formation of the bis(alkylthio)carbenium salt by addition of the acid onto the ketene dithioketal is reversible. On use of 4-substituted cyclohexylidene ketene dithioketals, the trans-substituted cyclohexane derivatives of the bis(alkylthio) carbenium salt, which are more thermodynamically favourable compared with the cis-configuration, and thus trans-substituted cyclohexane compounds containing a carboxylic acid orthoester fluoride function can therefore be obtained with very high selectivity.

For equilibration to give the thermodynamically more favourable isomer, it is therefore advantageous to stir the reaction mixture comprising ketene dithioketal, acid and corresponding carbenium salt for an extended time, in particular for from 15 minutes to 6 hours or even longer, at a temperature of from −80 to +50° C., in particular from −30 to +50° C.

The synthesis steps following the reaction of the ketene dithioketal are preferably carried out in situ, i.e. using the reaction mixture from the first reaction and thus without isolation of the carbenium salt.

According to a further process variant, the ketene dithioketal is obtained from a carbonyl compound. In order to obtain a ketene dithioketal of the formula IV, use is made of a carbonyl compound of the formula V

V

in which R and R' are as defined above.

R and R' may be linked to one another with formation of a cyclic group. Examples thereof are cyclohexanone and 4-substituted cyclohexanone derivatives.

The carbonyl compound may also have two or more carbonyl functions. Examples thereof are cyclohexane-1,4-dione and compounds containing 2 cyclohexanone groups. According to a first sub-variant, all carbonyl functions can be converted in accordance with the invention into ketene dithioketal functions and further into carboxylic acid orthoester fluoride functions. According to a second sub-variant, one or more carbonyl functions can be protected as the ketal before the reaction, with at least one carbonyl group remaining unprotected for conversion into the ketene dithioketal. The carboxylic acid orthoester fluorides accessible therefrom in accordance with the invention have one or more carbonyl functions, optionally protected as the ketal, in addition to the orthoester fluoride group. The free carbonyl function can advantageously be used to build up an optionally substituted alkyl, alkenyl or alkoxy group.

The ketene dithioketals are accessible in a simple manner and in high yields from the carbonyl compounds by processes known per se. Mention may be made here by way of example of D. J. Ager, Org. React. 1990, 38, 1–223, in particular pages 63, 95 and 96. It is advantageous that the carbonyl compounds may additionally contain acid-labile substituents, for example ketals or acetals, for masking of carbonyl functions. Furthermore, the ketene thioketals obtainable therefrom can generally be purified well due to their good crystallisation properties, but nevertheless have good solubility in the usual organic solvents.

A process which is preferred here is the reaction of a carbonyl compound with a 2-silyl-1,3-dithiane, which may be substituted. Particular preference is given here to the use of 2-trimethylsilyl-1,3-dithiane. The reaction is preferably carried out in the presence of a deprotonating compound, such as alkyllithium, for example n-butyllithium. An advantageous range for the reaction temperature is from −130 to 0° C. Suitable solvents are the solvents or mixtures indicated above.

Starting from the carbonyl compound of the formula V via the ketene dithioketal of the formula IV and the bis (alkylthio)carbenium salt of the formula II' obtainable by the addition reaction of the acid HY, the cyclic carboxylic acid orthoester fluoride of the formula I' can be prepared in accordance with the invention by reaction with the hydroxyl compound of the formula III and subsequent fluorodesulfurisation, as indicated in reaction scheme 1.

Reaction scheme 1:

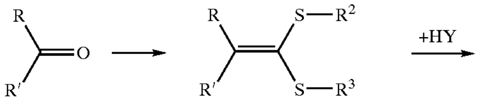

V IV

-continued

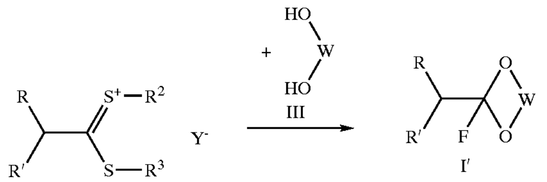

II'

I'

The formulae I' and II ' are identical with the formulae I and II respectively in the case where the group

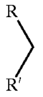

has the same meaning as $R^1$.

The entire conversion of the carbonyl compound of the formula V into the cyclic carboxylic acid orthoester fluoride of the formula I' is particularly preferably carried out as a so-called one-pot process, i.e. without isolation and purification of intermediates.

The present invention likewise relates to the cyclic carboxylic acid orthoester fluorides obtainable by the process according to the invention, in particular those of the formula I

I

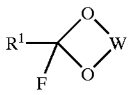

in which $R^1$ and W are as defined above.

The meaning of the formula I includes all isotopes of the chemical elements bound in the compounds of the formula I. If compounds of the formula I have one or more chiral centres, the formula I also covers enantiomerically pure and enriched forms in addition to the racemates. In enantiomerically pure or enriched form, the compounds of the formula I are also suitable as chiral dopants and in general for achieving chiral mesophases.

The radical $R^1$ preferably has the formula Ia $$R^a-(A-Z)_r- \quad \text{Ia}$$

in which $R^a$ is H, halogen, —CN, —NCS, —$SF_5$ or alkyl having from 1 to 12 carbon atoms, in which, in addition, one or two non-adjacent —$CH_2$— groups may be replaced by —O—, —S—, —CO—, —O—CO—, —CO—O—, -E- and/or —C≡C—, and/or in which, in addition, one or more H atoms may be replaced by halogen and/or —CN, E is $CR^4$=$CR^5$ or $CHR^4$—$CHR^5$, $R^4$ and $R^5$ are each, independently of one another, H, alkyl having 1–6 carbon atoms, F, Cl, Br, $CF_3$ or CN, Z is —O—CO—, —CO—O—, —$C_2H_4$—, —$CH_2$—$CF_2$—, —$CF_2$—$CH_2$—, —$CF_2$—$CF_2$—, —$(CF_2)_3$—, —$(CF_2)_4$—, —$CH_2$—O—, —$CF_2$—O—, —O—$CH_2$—, —O—$CF_2$—, —CH=CH—, —CF=CH—, —CH=CF—, —CF=CF—, —C≡C— or a single bond, A is 1,4-phenylene, in which one or more CH groups may be replaced by N, 1,4-cyclohexylene, in which one or two non-adjacent $CH_2$ groups may be replaced by O and/or S, 1,4-cyclo-hexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or optionally mono- or polyhalogenated alkyl having from 1 to 6 carbon atoms, and r is 0, 1, 2, 3 or 4, where groups A and/or Z which occur more than once may have identical or different meanings.

r is preferably greater than or equal to 1, in particular 1, 2 or 3.

Particularly preferred meanings of A are 1,4-phenylene, which may be monosubstituted, disubstituted or trisubstituted by fluorine, trans-1,4-cyclohexylene and 1,3-dioxane-2,5-diyl, for which, for reasons of simplicity, the abbreviations Phe, Cyc and Dio respectively are used below.

The term 1,3-dioxane-2,5-diyl in each case covers the two positional isomers

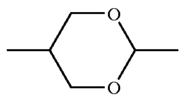

and

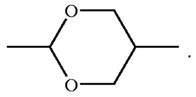

The following radicals $R^1$ of the sub-formulae Ia.1 to Ia.60 are preferred:

| | |
|---|---|
| $R^a$- | Ia.1 |
| $R^a$-Cyc- | Ia.2 |
| $R^a$-Phe- | Ia.3 |
| $R^a$-Dio- | Ia.4 |
| $R^a$-Cyc-Cyc- | Ia.5 |
| $R^a$-Cyc-Phe- | Ia.6 |
| $R^a$-Cyc-Dio- | Ia.7 |
| $R^a$-Phe-Cyc- | Ia.8 |
| $R^a$-Phe-Phe- | Ia.9 |
| $R^a$-Phe-Dio- | Ia.10 |
| $R^a$-Dio-Cyc- | Ia.11 |
| $R^a$-Dio-Phe- | Ia.12 |
| $R^a$-Cyc-Z-Cyc- | Ia.13 |
| $R^a$-Cyc-Z-Phe- | Ia.14 |
| $R^a$-Cyc-Z-Dio- | Ia.15 |
| $R^a$-Phe-Z-Cyc- | Ia.16 |
| $R^a$-Phe-Z-Phe- | Ia.17 |
| $R^a$-Phe-Z-Dio- | Ia.18 |
| $R^a$-Dio-Z-Cyc- | Ia.19 |
| $R^a$-Dio-Z-Phe- | Ia.20 |
| $R^a$-Cyc-Cyc-Cyc- | Ia.21 |
| $R^a$-Cyc-Cyc-Phe- | Ia.22 |
| $R^a$-Cyc-Cyc-Dio- | Ia.23 |
| $R^a$-Cyc-Phe-Cyc- | Ia.24 |
| $R^a$-Cyc-Phe-Phe- | Ia.25 |
| $R^a$-Cyc-Phe-Dio- | Ia.26 |
| $R^a$-Cyc-Dio-Cyc- | Ia.27 |
| $R^a$-Cyc-Dio-Phe- | Ia.28 |
| $R^a$-Phe-Cyc-Cyc- | Ia.29 |
| $R^a$-Phe-Cyc-Phe- | Ia.30 |
| $R^a$-Phe-Cyc-Dio- | Ia.31 |
| $R^a$-Phe-Phe-Cyc- | Ia.32 |
| $R^a$-Phe-Phe-Phe- | Ia.33 |
| $R^a$-Phe-Phe-Dio- | Ia.34 |
| $R^a$-Phe-Dio-Cyc- | Ia.35 |
| $R^a$-Phe-Dio-Phe- | Ia.36 |

-continued

| | |
|---|---|
| $R^a$-Dio-Cyc-Cyc- | Ia.37 |
| $R^a$-Dio-Cyc-Phe- | Ia.38 |
| $R^a$-Dio-Phe-Cyc- | Ia.39 |
| $R^a$-Dio-Phe-Phe- | Ia.40 |
| $R^a$-Cyc-Z-Cyc-Z-Cyc- | Ia.41 |
| $R^a$-Cyc-Z-Cyc-Z-Phe- | Ia.42 |
| $R^a$-Cyc-Z-Cyc-Z-Dio- | Ia.43 |
| $R^a$-Cyc-Z-Phe-Z-Cyc- | Ia.44 |
| $R^a$-Cyc-Z-Phe-Z-Phe- | Ia.45 |
| $R^a$-Cyc-Z-Phe-Z-Dio- | Ia.46 |
| $R^a$-Cyc-Z-Dio-Z-Cyc- | Ia.47 |
| $R^a$-Cyc-Z-Dio-Z-Phe- | Ia.48 |
| $R^a$-Phe-Z-Cyc-Z-Cyc- | Ia.49 |
| $R^a$-Phe-Z-Cyc-Z-Phe- | Ia.50 |
| $R^a$-Phe-Z-Cyc-Z-Dio- | Ia.51 |
| $R^a$-Phe-Z-Phe-Z-Cyc- | Ia.52 |
| $R^a$-Phe-Z-Phe-Z-Phe- | Ia.53 |
| $R^a$-Phe-Z-Phe-Z-Dio- | Ia.54 |
| $R^a$-Phe-Z-Dio-Z-Cyc- | Ia.55 |
| $R^a$-Phe-Z-Dio-Z-Phe- | Ia.56 |
| $R^a$-Dio-Z-Cyc-Z-Cyc- | Ia.57 |
| $R^a$-Dio-Z-Cyc-Z-Phe- | Ia.58 |
| $R^a$-Dio-Z-Phe-Z-Cyc- | Ia.59 |
| $R^a$-Dio-Z-Phe-Z-Phe- | Ia.60 |

Very particularly preferred meanings of $R^a$ are F, Cl, CN or alkyl or alkoxy having from 1 to 8 carbon atoms or alkenyl or alkenyloxy having from 2 to 8 carbon atoms, where the alkyl, alkoxy, alkenyl or alkenyloxy radicals may also be mono- to polyhalogenated, in particular fluorinated.

Preferred meanings of Z are —O—CO—, —CO—O—, —$C_2H_4$—, —$CF_2$—$CF_2$—, —$CH_2$—O—, —$CF_2$—O—, —O—$CH_2$—, —O—$CF_2$—, —CH═CH—, —C≡C— or a single bond.

The following groups W of the sub-formulae I.2a to I.2h are preferred:

I.2a

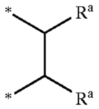

I.2b

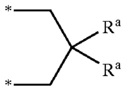

I.2c

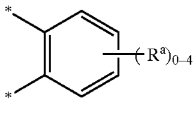

I.2d

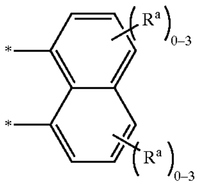

I.2e

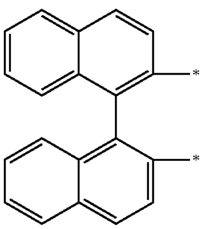

-continued

I.2f

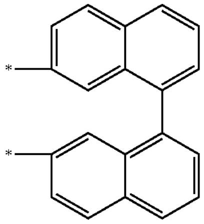

I.2g

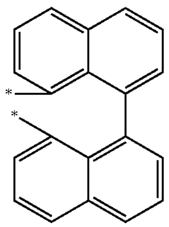

I.2h

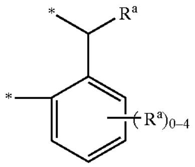

in which * indicates the bond to the orthoester fluoride group, and $R^a$ has the stated meaning and is preferably H, fluorine, chlorine, CN or optionally fluorinated and/or chlorinated alkyl having from 1 to 6 carbon atoms, and where the radicals $R^a$ which occur more than once may have identical or different meanings.

Particularly preferred meanings of the sub-formula I.2b are therefore

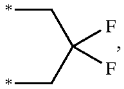

,

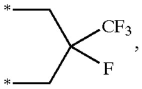

,

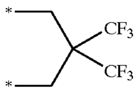

and

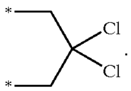

.

In the case of the meaning alkyl in the groups or substituents indicated above or below, in particular in R, R', $R^a$, $R^1$, $R^2$, $R^3$, $R^4$ and/or $R^5$, the alkyl radical may be linear or branched. It preferably has 1, 2, 3, 4, 5, 6, 7 or 8 carbon atoms. It is preferably linear and is therefore in particular methyl, ethyl, propyl, butyl, pentyl, hexyl, heptyl or octyl. A branched alkyl radical may be chiral or achiral. Preferred chiral alkyl radicals are 2-butyl (=1-methylpropyl), 2-methylbutyl, 2-methylpentyl, 3-methylpentyl, 2-ethylhexyl, 2-propylpentyl and 2-octyl. Preferred achiral alkyl radicals are isopropyl, isobutyl (=methylpropyl) and isopentyl (=3-methylbutyl). The alkyl radicals may be substituted in the manner indicated.

In the case of the meaning alkoxy in the groups or substituents indicated above or below, in particular in $R^a$, the alkoxy radical may be linear or branched. It is preferably linear and has 1, 2, 3, 4, 5, 6, 7 or 8 carbon atoms and is therefore in particular methoxy, ethoxy, propoxy, butoxy, pentoxy, hexyloxy, heptyloxy or octyloxy, furthermore nonyloxy, decyloxy, undecyloxy, dodecyloxy, tridecyloxy or tetradecyloxy.

In the case of the meaning alkenyl in the groups or substituents indicated above or below, in particular in $R^a$, the alkenyl radical may be straight-chain or branched. It is preferably straight-chain and has from 2 to 8 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, or oct-1-, -2-, -3-, -4-, -5-, -6- or -7-enyl.

In the case of the meaning alkenyloxy in the groups or substituents indicated above or below, in particular in $R^a$, the alkenyloxy radical may be straight-chain or branched. It is preferably straight-chain and accordingly is in particular vinyloxy, prop-1- or -2-enyloxy, but-1-, -2- or -3-enyloxy, pent-1-, -2-, -3- or -4-enyloxy, hex-1-, -2-, -3-, -4- or -5-enyloxy, hept-1-, -2-, -3-, -4-, -5- or -6-enyloxy, or oct-1-, -2-, -3-, -4-, -5-, -6- or -7-enyloxy.

The following working examples are intended to illustrate the invention without limiting it. Above and below, percentages are percent by weight. All temperatures are indicated in degrees Celsius. The abbreviation DBH is used for 1,3-dibromo-5,5-dimethylhydantoin.

WORKING EXAMPLES

Example 1

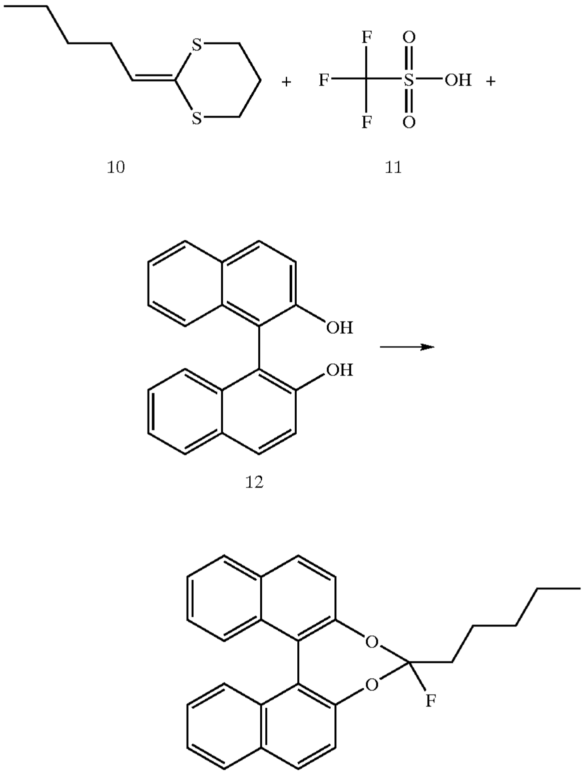

10 11 12 13

53.1 mmol of the thioacetal 10 are dissolved in 70 ml of dichloromethane, 53.1 mmol of trifluoromethanesulfonic acid 11 are slowly added with ice cooling, and the mixture is stirred for 30 minutes. The batch is subsequently cooled to −70° C., and a solution of 64.9 mmol of triethylamine and 23.9 mmol of (−)-S-1,1'-bi(2-naphthol) 12 in 50 ml of dichloromethane is added dropwise over the course of 15 minutes. After a further 45 minutes, 265.5 mmol of triethylamine trishydrofluoride are added slowly, and a suspension of 265.5 mmol of DBH in 120 ml of dichloromethane is then added in portions over the course of 60 minutes. The batch is stirred for a further 90 minutes and warmed to −20° C., and the orange suspension is carefully added to an ice-cold mixture of 1 l of approximately 1M sodium hydroxide solution and 100 ml of sodium hydrogensulfite solution. The aqueous phase is separated off and extracted three times with dichloromethane, and the combined organic phases are subjected to conventional work-up.

The product has a melting point of about 138° C. Mass-spectrometric and NMR analysis show the expected signals.

Example 2

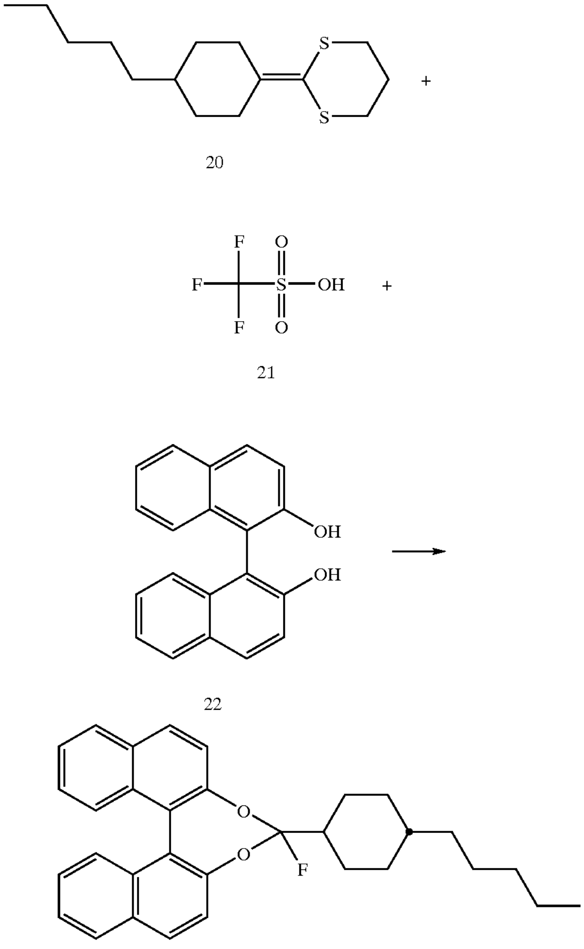

20 21 22 23

37.0 mmol of the thioacetal 20 are dissolved in 50 ml of dichloromethane, and 37.0 mmol of trifluoromethanesulfonic acid 21 are slowly added with ice cooling. After 40 minutes, the cooling is removed, and the yellow solution is stirred at 20° C. for a further 50 minutes. The batch is subsequently cooled to −70° C., and a solution of 37.0 mmol of triethylamine and 16.6 mmol of (−)-S-1,1'-bi(2-naphthol) 22 in 30 ml of dichloromethane is added dropwise. After 90 minutes, 155 mmol of triethylamine trishydrofluoride are slowly added, and a suspension of 184.8 mmol of DBH in 80 ml of dichloromethane is then added in portions over the course of 45 minutes. After 60 minutes, the batch is allowed to warm to −20° C., and the orange suspension is carefully added to an ice-cold mixture of 1 l of approximately 1M sodium hydroxide solution and 100 ml of sodium hydrogensulfite solution. The aqueous phase is separated off and extracted three times with pentane, and the combined organic phases are subjected to conventional work-up. The product has a melting point of about 143° C. Mass-spectrometric and NMR analysis give the expected signals.

Example 3

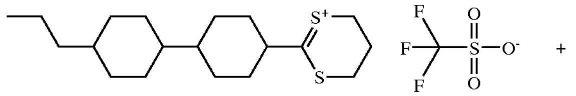

30

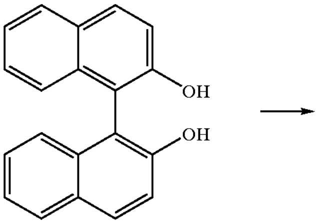

31

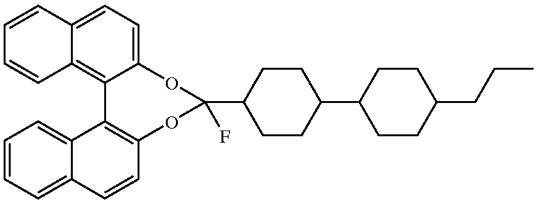

32

76.8 mmol of the dithianylium triflate 30 are introduced into 300 ml of dichloromethane, and a solution of 34.9 mmol of R-(+)-1,1'-bi(2-naphthol) 31 and 38.4 mmol of triethylamine in 50 ml of dichloromethane is added dropwise at −65° C. The mixture is stirred for a further 90 minutes, triethylamine trishydrofluoride (0.38 mol) is slowly added, and a suspension of 0.38 mol of DBH in 150 ml of dichloromethane is then added in portions over the course of 40 minutes. After 60 minutes, the batch is allowed to warm to −20° C., and the orange suspension is carefully added to an ice-cold mixture of 1.5 l of 1M sodium hydroxide solution and 150 ml of sodium hydrogensulfite solution. The aqueous phase is separated off and extracted three times with dichloromethane, and the combined organic phases are subjected to conventional work-up. Mass-spectrometric and NMR analysis give the expected signals.

Example 4

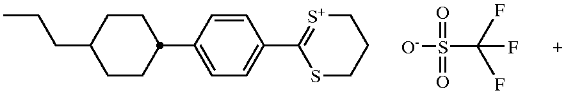

40

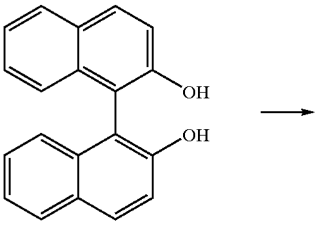

41

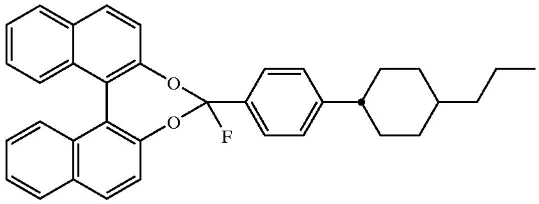

42

34.9 mmol of S-(−)-1,1'-bi(2-naphthol) 41 are introduced into 120 ml of dichloromethane. 76.8 mmol of triethylamine are added, and a solution of 34.9 mmol of the dithianylium triflate 40 in 80 ml of dichloromethane are added dropwise over the course of 1 hour at −65° C. The mixture is stirred for a further 1 hour, 0.15 mol of triethylamine trishydrofluoride is added slowly, and a suspension of 0.105 mol of DBH in 50 ml of dichloromethane is then added in portions over the course of 90 minutes. After 60 minutes, the batch is allowed to warm to −20° C., and the orange suspension is carefully added to an ice-cold mixture of 500 ml of 1M sodium hydroxide solution and 50 ml of sodium hydrogensulfite solution (pH=7). The aqueous phase is separated off and extracted three times with dichloromethane, and the combined organic phases are subjected to conventional work-up. The product has a melting point of about 228° C. Mass-spectrometric and NMR analysis give the expected signals.

The following compounds, defined by the group W and the radical $R^1$ in the formula I, are obtained analogously to the above working examples:

| No. | W | $R^1$ |
|---|---|---|
| 50 | 1,1'-Binaphthalene-2,2'-diyl | $-C_3H_7$ |
| 51 | 1,1'-Binaphthalene-2,2'-diyl | $-C_4H_9$ |
| 52 | 1,1'-Binaphthalene-2,2'-diyl | $-C_6H_{13}$ |
| 53 | 1,1'-Binaphthalene-2,2'-diyl | 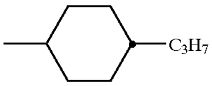 |
| 54 | 1,1'-Binaphthalene-2,2'-diyl | 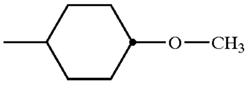 |

-continued
| No. | W | $R^1$ |
|---|---|---|
| 55 | 1,1'-Binaphthalene-2,2'-diyl | 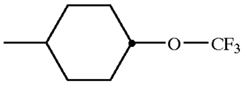 |
| 56 | 1,1'-Binaphthalene-2,2'-diyl | 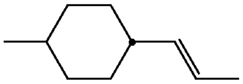 |
| 57 | 1,1'-Binaphthalene-2,2'-diyl | 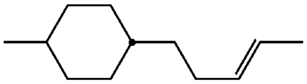 |
| 58 | 1,1'-Binaphthalene-2,2'-diyl | 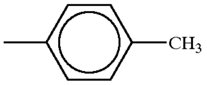 |
| 59 | 1,1'-Binaphthalene-2,2'-diyl | 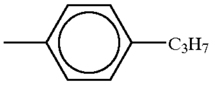 |
| 60 | 1,1'-Binaphthalene-2,2'-diyl | 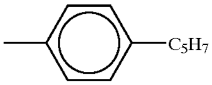 |
| 61 | 1,1'-Binaphthalene-2,2'-diyl | 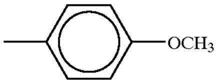 |
| 62 | 1,1'-Binaphthalene-2,2'-diyl | 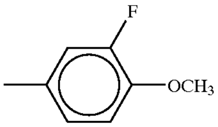 |
| 63 | 1,1'-Binaphthalene-2,2'-diyl | 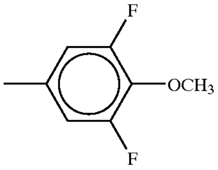 |
| 64 | 1,1'-Binaphthalene-2,2'-diyl | 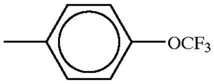 |
| 65 | 1,1'-Binaphthalene-2,2'-diyl | 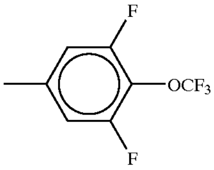 |
| 66 | 1,1'-Binaphthalene-2,2'-diyl | 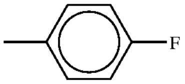 |
| 67 | 1,1'-Binaphthalene-2,2'-diyl | 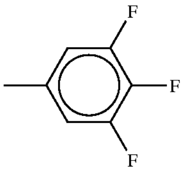 |

-continued
| No. | W | R¹ |
|---|---|---|
| 68 | 1,1'-Binaphthalene-2,2'-diyl | 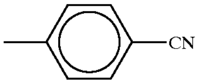 |
| 69 | 1,1'-Binaphthalene-2,2'-diyl | 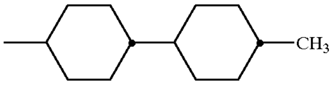 |
| 70 | 1,1'-Binaphthalene-2,2'-diyl | 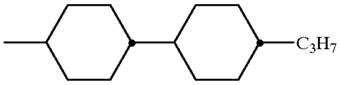 |
| 71 | 1,1'-Binaphthalene-2,2'-diyl | 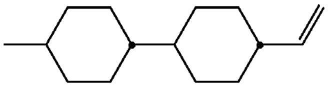 |
| 72 | 1,1'-Binaphthalene-2,2'-diyl | 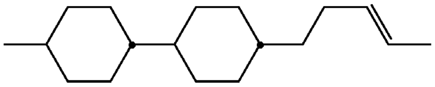 |
| 73 | 1,1'-Binaphthalene-2,2'-diyl | 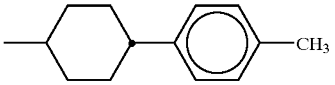 |
| 74 | 1,1'-Binaphthalene-2,2'-diyl | 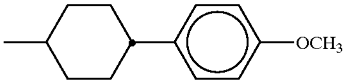 |
| 75 | 1,1'-Binaphthalene-2,2'-diyl | 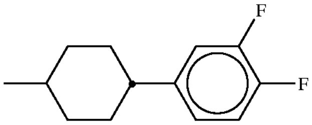 |
| 76 | 1,1'-Binaphthalene-2,2'-diyl | 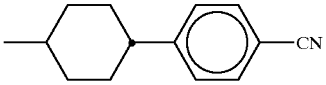 |
| 77 | 1,1'-Binaphthalene-2,2'-diyl | 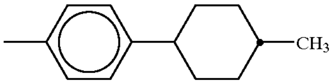 |
| 78 | 1,1'-Binaphthalene-2,2'-diyl | 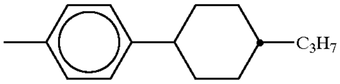 |
| 79 | 1,1'-Binaphthalene-2,2'-diyl | 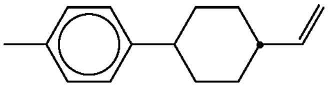 |
| 80 | 1,1'-Binaphthalene-2,2'-diyl | 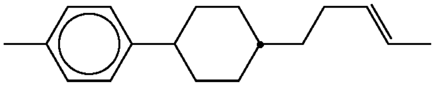 |
| 81 | 1,1'-Binaphthalene-2,2'-diyl | 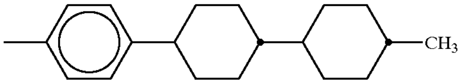 |
| 82 | 1,1'-Binaphthalene-2,2'-diyl | 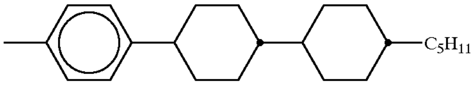 |

-continued

| No. | W | $R^1$ |
|---|---|---|
| 83 | 1,1'-Binaphthalene-2,2'-diyl | 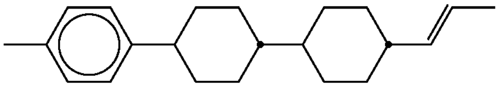 |
| 84 | 1,1'-Binaphthalene-2,2'-diyl | 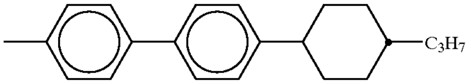 |
| 85 | 1,1'-Binaphthalene-2,2'-diyl | 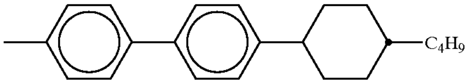 |
| 86 | 1,1'-Binaphthalene-7,7'-diyl | $—C_3H_7$ |
| 87 | 1,1'-Binaphthalene-7,7'-diyl | $—C_5H_{11}$ |
| 88 | 1,1'-Binaphthalene-7,7'-diyl | 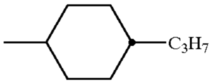 |
| 89 | 1,1'-Binaphthalene-7,7'-diyl | 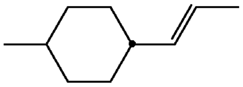 |
| 90 | 1,1'-Binaphthalene-7,7'-diyl | 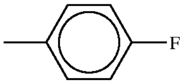 |
| 91 | 1,1'-Binaphthalene-7,7'-diyl | 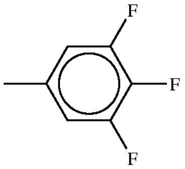 |
| 92 | 1,1'-Binaphthalene-7,7'-diyl | 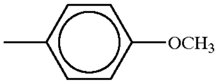 |
| 93 | 1,1'-Binaphthalene-7,7'-diyl | 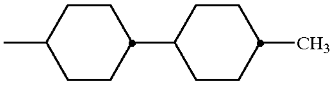 |
| 94 | 1,1'-Binaphthalene-7,7'-diyl | 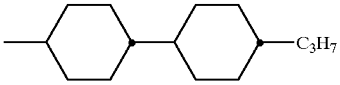 |
| 95 | 1,1'-Binaphthalene-7,7'-diyl | 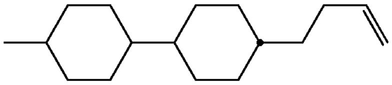 |
| 96 | 1,1'-Binaphthalene-7,7'-diyl | 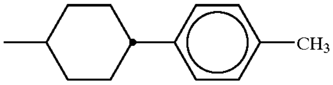 |
| 97 | 1,1'-Binaphthalene-7,7'-diyl | 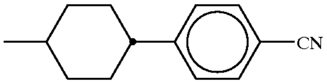 |
| 98 | 1,1'-Binaphthalene-7,7'-diyl | 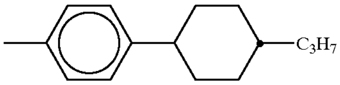 |

-continued

| No. | W | $R^1$ |
|---|---|---|
| 99 | 1,1'-Binaphthalene-7,7'-diyl | 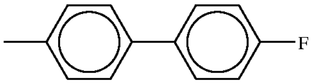 |
| 100 | 1,1'-Binaphthalene-7,7'-diyl | 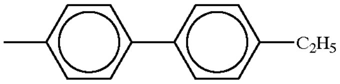 |
| 101 | 1,1'-Binaphthalene-7,7'-diyl | 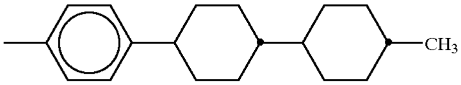 |
| 102 | 1,1'-Binaphthalene-7,7'-diyl | 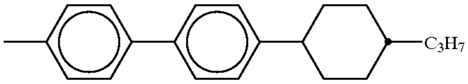 |
| 103 | 1,1'-Binaphthalene-8,8'-diyl | $—C_4H_9$ |
| 104 | 1,1'-Binaphthalene-8,8'-diyl | $—C_7H_{15}$ |
| 105 | 1,1'-Binaphthalene-8,8'-diyl | 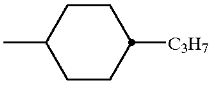 |
| 106 | 1,1'-Binaphthalene-8,8'-diyl | 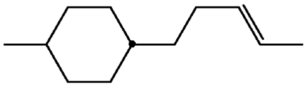 |
| 107 | 1,1'-Binaphthalene-8,8'-diyl | 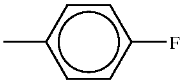 |
| 108 | 1,1'-Binaphthalene-8,8'-diyl | 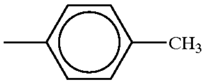 |
| 109 | 1,1'-Binaphthalene-8,8'-diyl | 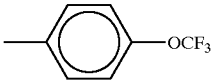 |
| 110 | 1,1'-Binaphthalene-8,8'-diyl | 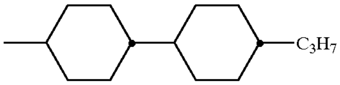 |
| 111 | 1,1'-Binaphthalene-8,8'-diyl | 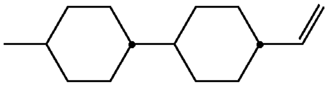 |
| 112 | 1,1'-Binaphthalene-8,8'-diyl | 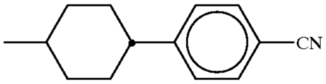 |
| 113 | 1,1'-Binaphthalene-8,8'-diyl | 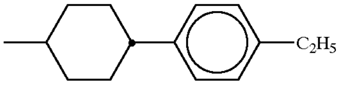 |
| 114 | 1,1'-Binaphthalene-8,8'-diyl | 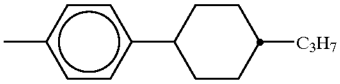 |
| 115 | 1,1'-Binaphthalene-8,8'-diyl | 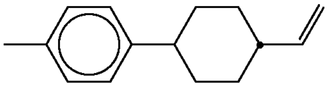 |

-continued
| No. | W | $R^1$ |
|---|---|---|
| 116 | 1,1'-Binaphthalene-8,8'-diyl | 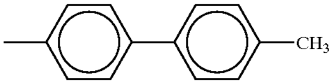 |
| 117 | 1,1'-Binaphthalene-8,8'-diyl | 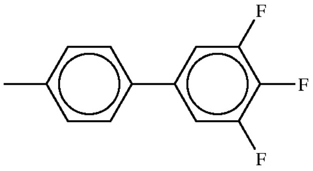 |
| 118 | 1,1'-Binaphthalene-8,8'-diyl | 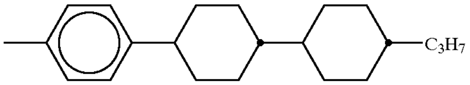 |
| 119 | 1,1'-Binaphthalene-8,8'-diyl | 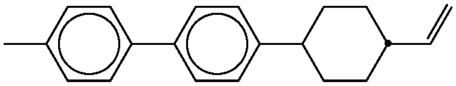 |
| 120 | 1,2-Phenylene | $-C_5H_{11}$ |
| 121 | 1,2-Phenylene | 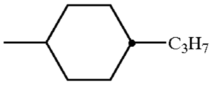 |
| 122 | 1,2-Phenylene | 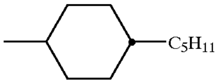 |
| 123 | 1,2-Phenylene | 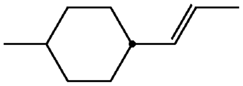 |
| 124 | 1,2-Phenylene | 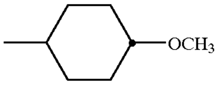 |
| 125 | 1,2-Phenylene | 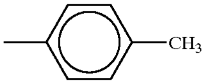 |
| 126 | 1,2-Phenylene | 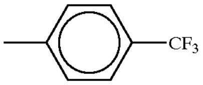 |
| 127 | 1,2-Phenylene | 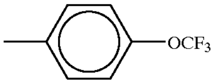 |
| 128 | 1,2-Phenylene | 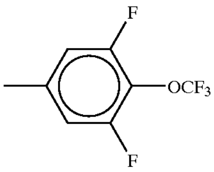 |
| 129 | 1,2-Phenylene | 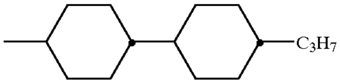 |

-continued
| No. | W | $R^1$ |
|---|---|---|
| 130 | 1,2-Phenylene | 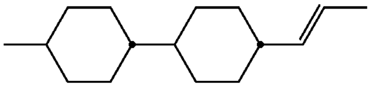 |
| 131 | 1,2-Phenylene | 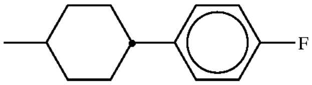 |
| 132 | 1,2-Phenylene | 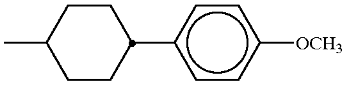 |
| 133 | 1,2-Phenylene | 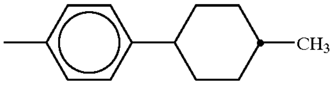 |
| 134 | 1,2-Phenylene | 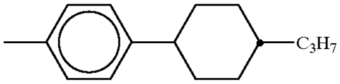 |
| 135 | 1,2-Phenylene | 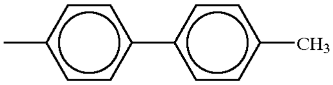 |
| 136 | 1,2-Phenylene | 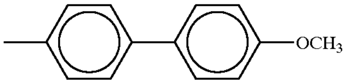 |
| 137 | 1,2-Phenylene | 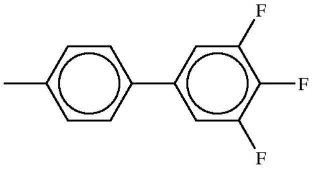 |
| 138 | 1,2-Phenylene | 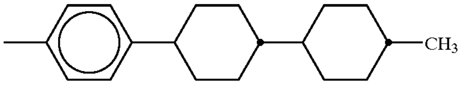 |
| 139 | 4-Fluoro-1,2-phenylene | 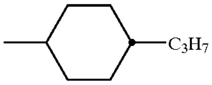 |
| 140 | 4-Fluoro-1,2-phenylene | 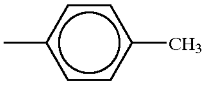 |
| 141 | 4-Fluoro-1,2-phenylene | 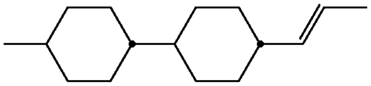 |
| 142 | 4-Fluoro-1,2-phenylene | 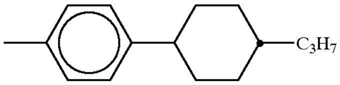 |
| 143 | 4-Fluoro-1,2-phenylene | 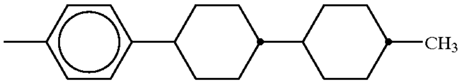 |
| 144 | 1,1'-Biphenyl-2,2'-diyl | —$C_5H_{11}$ |

-continued
| No. | W | $R^1$ |
|---|---|---|
| 145 | 1,1'-Biphenyl-2,2'-diyl | 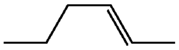 |
| 146 | 1,1'-Biphenyl-2,2'-diyl | 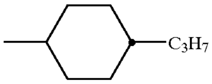 |
| 147 | 1,1'-Biphenyl-2,2'-diyl | 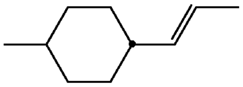 |
| 148 | 1,1'-Biphenyl-2,2'-diyl | 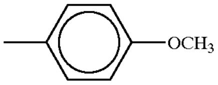 |
| 149 | 1,1'-Biphenyl-2,2'-diyl | 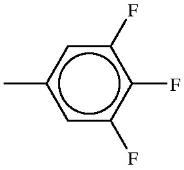 |
| 150 | 1,1'-Biphenyl-2,2'-diyl | 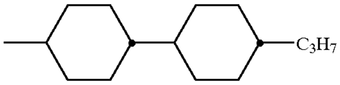 |
| 151 | 1,1'-Biphenyl-2,2'-diyl | 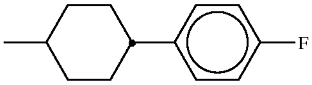 |
| 152 | 1,1'-Biphenyl-2,2'-diyl | 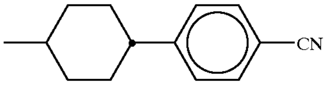 |
| 153 | 1,1'-Biphenyl-2,2'-diyl | 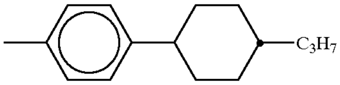 |
| 154 | 1,1'-Biphenyl-2,2'-diyl | 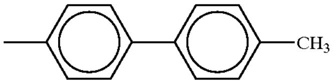 |
| 155 | 1,1'-Biphenyl-2,2'-diyl | 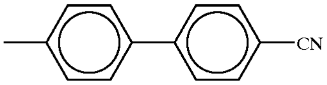 |
| 156 | 1,1'-Biphenyl-2,2'-diyl | 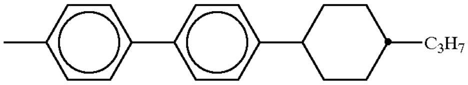 |
| 157 | 1-Methylbenzene-1,2-diyl | $-C_5H_{11}$ |
| 158 | 1-Methylbenzene-1,2-diyl | 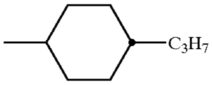 |
| 159 | 1-Methylbenzene-1,2-diyl | 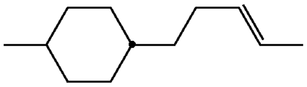 |

-continued

| No. | W | $R^1$ |
|---|---|---|
| 160 | 1-Methylbenzene-1,2-diyl | 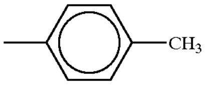 |
| 161 | 1-Methylbenzene-1,2-diyl | 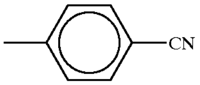 |
| 162 | 1-Methylbenzene-1,2-diyl | 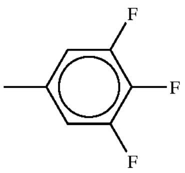 |
| 163 | 1-Methylbenzene-1,2-diyl | 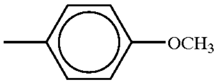 |
| 164 | 1-Methylbenzene-1,2-diyl | 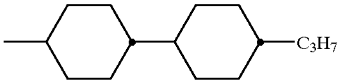 |
| 165 | 1-Methylbenzene-1,2-diyl | 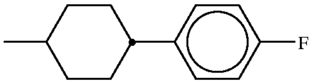 |
| 166 | 1-Methylbenzene-1,2-diyl | 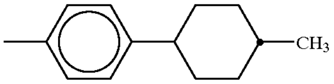 |
| 167 | 1-Methylbenzene-1,2-diyl | 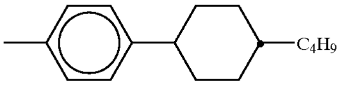 |
| 168 | 1-Methylbenzene-1,2-diyl | 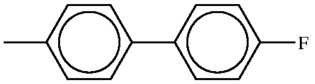 |
| 169 | 1-Methylbenzene-1,2-diyl | 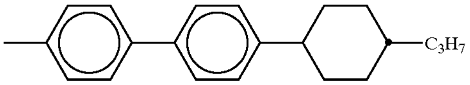 |

What is claimed is:

1. A process for preparing a cyclic carboxylic acid orthoester fluoride, comprising reacting:

a) at least one bis(alkylthio)carbenium salt with at least one organic compound containing at least two hydroxyl groups in the presence of at least one base, b) and subsequently, subjecting to oxidative fluoride sulfurisation using a fluorinating agent and an oxidant the resultant thioorthoester to give the cyclic carboxylic acid orthoester fluoride.

2. A process according to claim 1, wherein a bis(alkylthio) carbenium salt is of the formula II

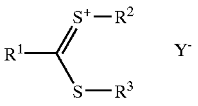

II wherein $R^1$ is a straight-chain, branched or cyclic alkyl having from 1–25 carbon atoms, wherein one or more H atoms may be replaced by halogen, —CN or further optionally substituted alkyl and/or aryl radicals, and/or wherein one or more non-adjacent —$CH_2$— groups may be replaced, independently of one another, by —CO—, —O—CO—, —CO—O—, —O—, —S—, —CH=CH—, —C≡C—, —NH— or —$N(CH_3)$—, and/or aryl, which may be monosubstituted or polysubstituted by halogen or straight-chain, branched and/or cyclic alkyl and/or aryl, and wherein one or more CH groups may be replaced by N or O, $R^2$ and $R^3$, independently of one another, are straight-chain, branched or cyclic alkyl having from 1–12 carbon atoms, where $R^2$ and $R^3$ may be bridged to one another in such a way that the group

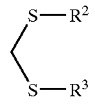

is a 4- to 8-membered ring, and/or wherein one or more H atoms may be replaced by halogen or further optionally substituted alkyl and/or aryl radicals, and/or wherein one or more non-adjacent —$CH_2$— groups may be replaced, independently of one another, by —CO—, —O—, —S—, —CH=CH—, —C≡C—, —NH— or —$N(CH_3)$—, and/or aryl, which may be monosubstituted or polysubstituted by halogen or straight-chain, branched and/or cyclic alkyl and/or aryl, and $Y^-$ is a non-coordinating or weakly coordinating anion, and the organic compound containing at least two hydroxyl groups of the formula III

III

wherein

W is a straight-chain, branched or cyclic alkylene group having 2 or more carbon atoms, wherein one or more H atoms may be replaced by halogen or further optionally substituted alkyl and/or aryl radicals, and/or wherein one or more non-adjacent —$CH_2$— groups may be replaced, independently of one another, by —CO—, —O—, —S—, —CH=CH—, —C≡C—, —NH— or —$N(CH_3)$—, and/or an arylene group, which may be monosubstituted or polysubstituted by halogen or straight-chain, branched and/or cyclic alkyl and/or aryl, and wherein one or more CH groups may be replaced by N or O, to give a cyclic carboxylic acid orthoester fluoride of the formula I

I

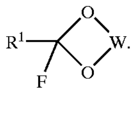

3. A process according to claim 1, wherein the oxidative fluorodesulfurisation is in situ.

4. A process according to claim 2, wherein that the oxidative fluorodesulfurisation is in situ.

5. A process according to claim 1, wherein the organic compound containing at least two hydroxyl groups is an alkanediol, an aromatic or heteroaromatic dihydroxyl compound or a hydroxyalkylphenol, each of which may be substituted by one or more halogen atoms and/or alkyl groups.

6. A process according to claim 2, wherein $Y^-$ is a halide, tetrafluoroborate, hexafluorophosphate, perchlorate or alkyl- or arylcarboxylate or alkyl- or arylsulfonate anion, where one, a number or all of the H atoms in the alkyl or aryl groups may be substituted by fluorine or chlorine.

7. A process according to claim 1, wherein the oxidant is a compound which liberates halonium equivalents.

8. A process according to claim 1, wherein the fluorinating agent is selected from the group formed by hydrogen fluoride, aliphatic and aromatic amine/hydrogen fluoride complexes, in particular selected from the group formed by pyridine, triethylamine, melamine and polyvinylpyridine/hydrogen fluoride complexes.

9. A process according to claim 1, wherein the bis(alkylthio)carbenium salt is employed in a molar ratio of less than or equal 2:1, to the organic compound containing at least two hydroxyl groups.

10. A process according to claim 1, wherein the bis(alkylthio)carbenium salt is obtained by addition of an acid onto a ketene dithioketal.

11. A process according to claim 2, wherein the bis(alkylthio)carbenium salt is obtained by addition of an acid onto a ketene dithioketal, wherein the bis(alkylthio) carbenium salt of the formula II is obtained by addition of an acid HY, onto a ketene dithioketal of the formula IV

IV

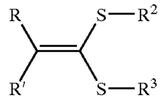

and

R and R', independently of one another, are as defined for $R^1$, including H, in such a way that the

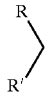

group has the same meaning as $R^1$.

12. A process according to claim 10, wherein the ketene dithioketal is obtained from a carbonyl compound by reaction with one or more thiol compounds.

13. A process according to claim 1, wherein the oxidant is dimethyldibromohydantoin, N-chlorosuccinimide, N-bromosuccinimide, N-iodosuccinimide, dibromoisocyanuric acid, chlorine, bromine, $SO_2Cl_3$, $SO_2ClF$, a nitrosonium, a nitronium salt, an organic or inorganic nitrite or chloramine-T.

14. A process according to claim 1, wherein the fluorinating agent is pyridine, triethylamine, melamine, or a polyvinylpyridine/hydrogen fluoride complex.

15. A process according to claim 1, wherein the bis(alkythio)carbenium salt is employed in a molar ratio of less than or equal to 1.3:1, to the organic compound containing at least two hydroxyl groups.

* * * * *

UNITED STATES PATENT AND TRADEMARK OFFICE

CERTIFICATE OF CORRECTION

PATENT NO. : 6,916,940 B2
DATED : July 12, 2005
INVENTOR(S) : Peer Kirsch

It is certified that error appears in the above-identified patent and that said Letters Patent is hereby corrected as shown below:

Column 29,
Line 66, reads “wherein a bis” should read -- wherein the bis --.

Column 30,
Line 64, delete the word “from”.

Column 31,
Line 30, reads “groups of” should read -- groups is of --.
Line 62, delete “that”.

Column 32,
Line 15, reads “complexes in particular selected from the group formed by pyridine, triethylamine, melamine and polyvinylpyridine/hydrogen fluoride complexes.” should read -- complexes. --.
Line 54, reads “Cl3” should read -- Cl2 --.

Signed and Sealed this

Thirteenth Day of December, 2005

JON W. DUDAS
*Director of the United States Patent and Trademark Office*